United States Patent
Hung et al.

(10) Patent No.: US 9,187,452 B1
(45) Date of Patent: Nov. 17, 2015

(54) METHOD FOR PREPARING NILOTINIB

(71) Applicant: FORMOSA LABORATORIES, INC., Taoyuan (TW)

(72) Inventors: Jui-Te Hung, Taoyuan (TW); Wen-Chin Chen, Taoyuan (TW)

(73) Assignee: FORMOSA LABORATORIES, INC., Taoyuan (TW)

( * ) Notice: Subject to any disclaimer, the term of this patent is extended or adjusted under 35 U.S.C. 154(b) by 0 days.

(21) Appl. No.: 14/479,318

(22) Filed: Sep. 7, 2014

(51) Int. Cl.
*C07D 401/14* (2006.01)
(52) U.S. Cl.
CPC .................................. *C07D 401/14* (2013.01)
(58) Field of Classification Search
CPC ..................................................... C07D 401/14
See application file for complete search history.

(56) References Cited

PUBLICATIONS

Duveau, D. Y.,"Synthesis and biological evaluation of analogues of the kinase inhibitor nilotinib as Abl and Kit inhibitors." Bioorganic & medicinal chemistry letters 23.3 (2013): 682-686.*

* cited by examiner

*Primary Examiner* — Samantha Shterengarts
*Assistant Examiner* — Matt Mauro
(74) *Attorney, Agent, or Firm* — Hannah M. Tien

(57) ABSTRACT

The present invention provides a method for preparing Nilotinib of the following structure:

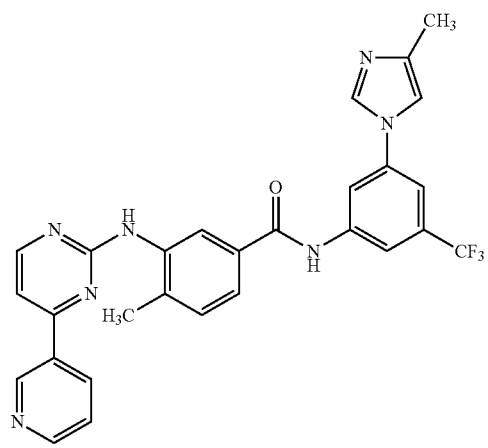

by direct condensation of an ester and an aniline promoted by trialkyl aluminum in an organic solvent.

5 Claims, 1 Drawing Sheet

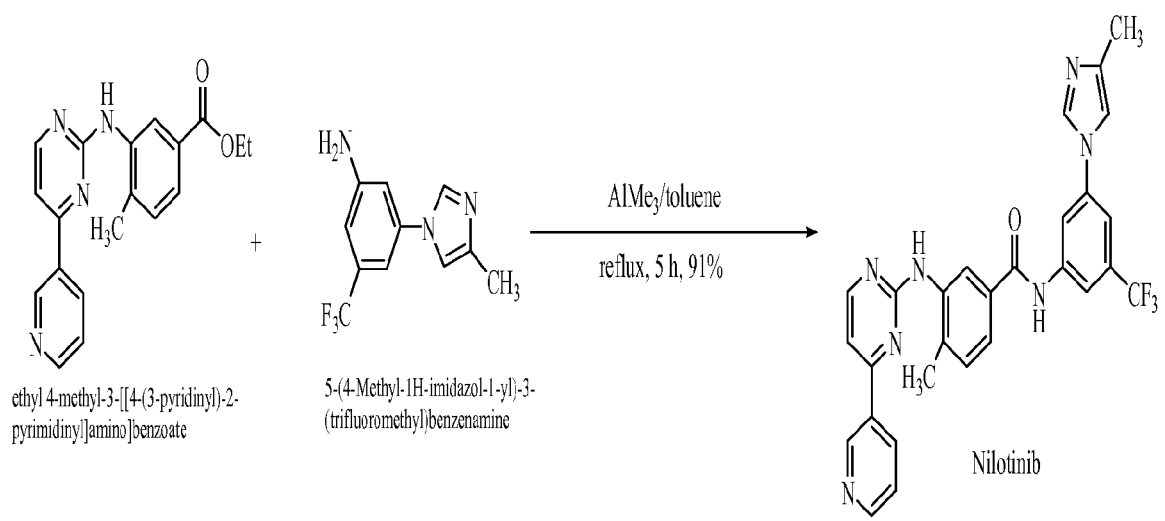

METHOD FOR PREPARING NILOTINIB

FIELD OF THE INVENTION

The present invention relates to a novel method for preparing Nilotinib by coupling an ester with aniline using trialkyl aluminum compound as the coupling reagent.

BACKGROUND OF THE INVENTION

Nilotinib, or 4-methyl-3-[[4-(3-pyridinyl)-2-pyrimidinyl]amino]-N-[5-(4-methyl-1H-imidazol-1-yl)-3-(trifluoromethyl)phenyl]benzamide, of the following structure is a small molecule tyrosine kinase inhibitor which can be used for the treatment of certain neoplastic diseases, such as Philadelphia Chromosome Chronic myelogenous leukemia.

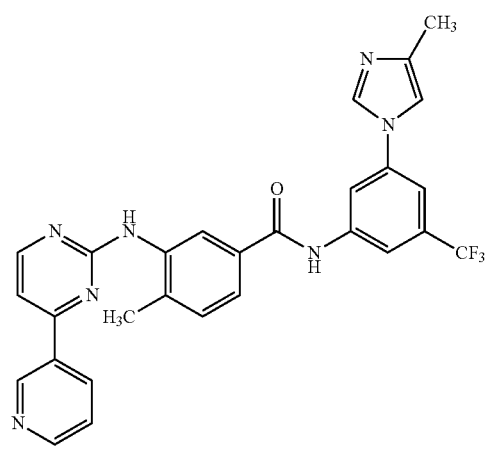 [SMILES: Cc1cn(-c2cc(NC(=O)c3ccc(C)c(Nc4nccc(-c5cccnc5)n4)c3)cc(C(F)(F)F)c2)cn1]

The method for the preparation of Nilotinib was first disclosed in the U.S. Pat. No. 7,169,791 B2 (the '791 patent), which involves the coupling of an acid, 4-methyl-3[[4-(3-pyridinyl)-2-pyrimidinyl]amino]benzoic acid, with an aniline derivative 5-(4-methyl-1H-imidazol-1-yl)-3-(trifluoromethyl)benzenamine using excessive diethyl cyanophosphonate as a coupling reagent.

The general reaction scheme of the process disclosed by the '791 patent is illustrated as follows:

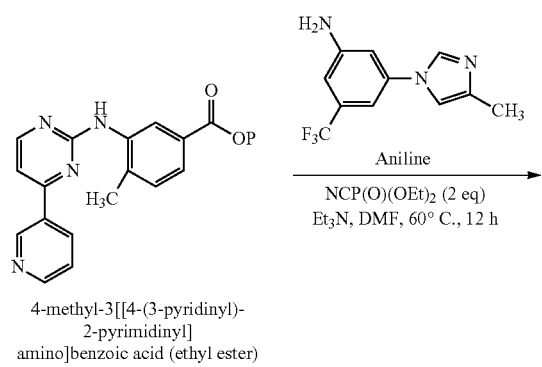

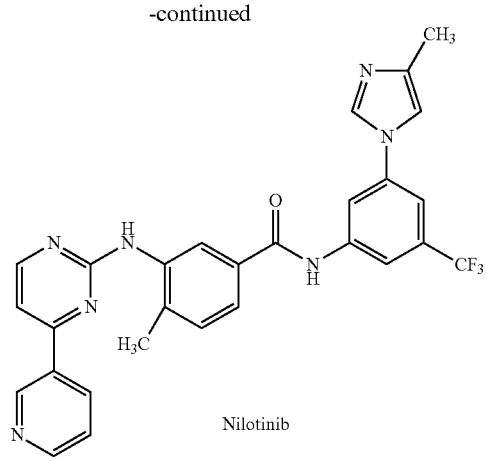

Nilotinib

This process, however, gives low and inconsistent yields and the coupling reagent, diethyl cyanophosphonate, is an expensive reagent.

An improved process for the preparation of Nilotinib was later disclosed by the U.S. Patent 2008/0188656 (the '656 patent). The general reaction scheme of this improved process is illustrated as follows:

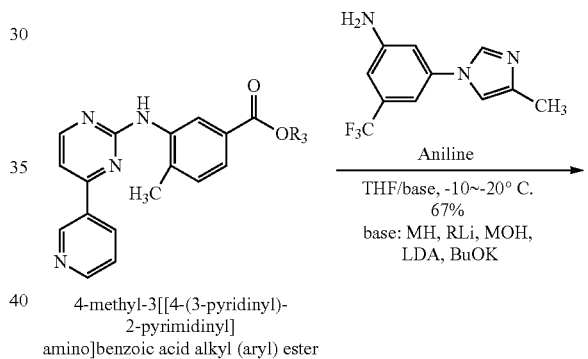

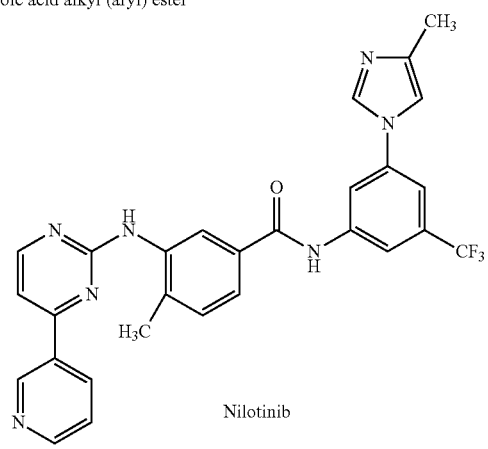

Nilotinib

According to the '656 patent, Nilotinib is prepared by direct condensation of an ester derivative with the same aniline molecule disclosed in the '791 patent. The reaction is catalyzed by a strong base and carried out in an organic solvent. When the strong base potassium tert-Butoxide is used as the coupling reagent in solvent tetrahydrofuran, a free base Nilotinib can be produced in reasonable yield.

This improved process is repeatable at temperatures ranging from 0~40° C. and Nilotinib can be obtained after 22 hours at 75% conversion. Detail results are shown in Table 1.

TABLE 1

Coupling reaction by reagent t-BuOK in THF

| Entry | Eq. of Ester/amine | Coupling Reagent | Temp. (° C.) | Time (h) | Nilotinib (Area %) (By HPLC) |
|---|---|---|---|---|---|
| Patent '791 | 1.0/1.0 | t-BuOK (5.5 eq.) | 18-23 | NA | 67% (Isolate) |
| 1 | 1.0/1.0 | t-BuOK (5.5 eq.) | 0 | 1.0 | 75.7 |
|  |  |  | 0 | 3.0 | 73.0 |
|  |  |  | 0 | 6.0 | 73.9 |
|  |  |  | 0 | 22.0 | 75.1 |
| 2 | 1.0/1.0 | t-BuOK (5.5 eq.) | 20 | 1.0 | 72.3 |
|  |  |  | 20 | 3.0 | 72.4 |
|  |  |  | 20 | 6.0 | 72.5 |
|  |  |  | 20 | 22.0 | 75.1 |
| 3 | 1.0/1.0 | t-BuOK (5.5 eq.) | 40 | 1.0 | 72.2 |
|  |  |  | 40 | 3.0 | 71.8 |
|  |  |  | 40 | 6.0 | 74.3 |
|  |  |  | 40 | 22.0 | 74.9 |

SUMMARY OF THE INVENTION

A method for preparing Nilotinib of the following structure:

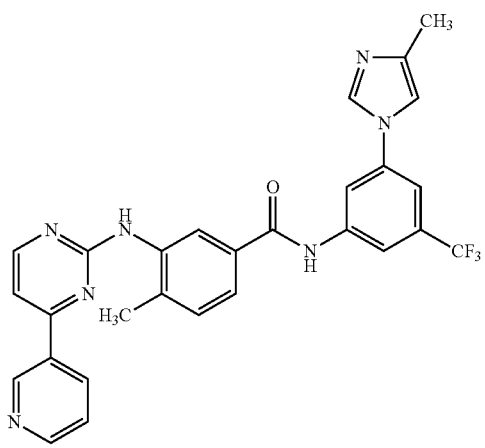 [SMILES: Cc1cn(-c2cc(NC(=O)c3ccc(C)c(Nc4nccc(-c5cccnc5)n4)c3)cc(C(F)(F)F)c2)cn1]

comprising reacting an ester of the following structure:

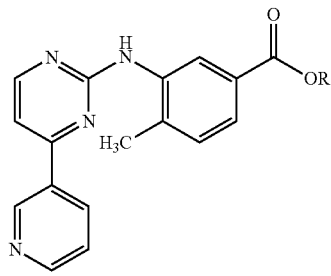

with the compound 5-(4-methyl-1H-imidazol-1-yl)-3-(trifluoromethyl)-benzenamine of the following structure:

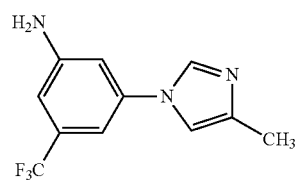

wherein R is lower alkyl, phenyl, phenyl-lower alkyl or substituted phenyl, wherein the method is promoted by a trialkyl aluminum compound in an organic solvent.

BRIEF DESCRIPTION OF THE DRAWINGS

FIG. 1 illustrates the general reaction scheme of the present invention.

DETAILED DESCRIPTION OF THE INVENTION

The present invention provides a novel method for coupling an ester with an aniline using trialkyl aluminum compound as the coupling reagent, which produces Nilotinib in high yields and high purity. The general reaction scheme of the present invention is illustrated as follows:

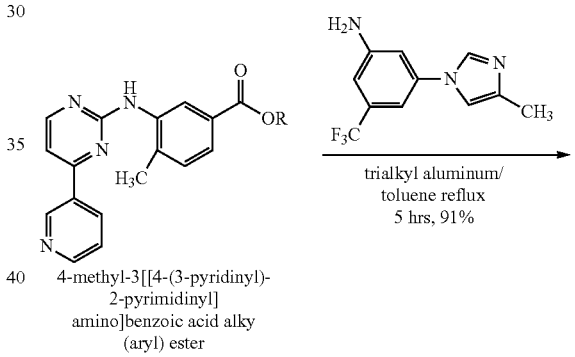

4-methyl-3[[4-(3-pyridinyl)-2-pyrimidinyl]amino]benzoic acid alky (aryl) ester

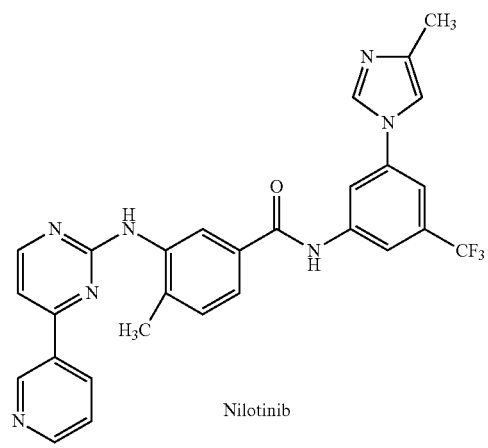

Nilotinib

In one embodiment of the present invention, the method for preparing Nilotinib of the following structure:

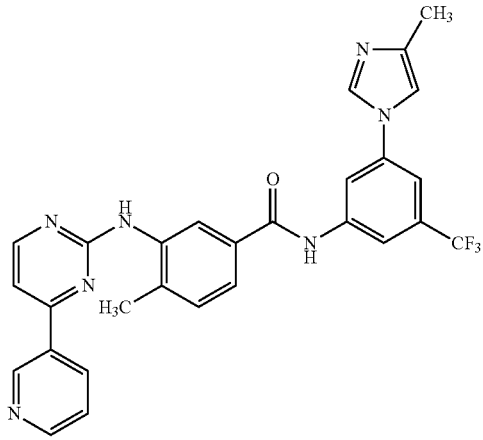 [SMILES: Cc1cn(-c2cc(NC(=O)c3ccc(C)c(Nc4nccc(-c5cccnc5)n4)c3)cc(C(F)(F)F)c2)cn1]

comprising reacting an ester of the following structure:

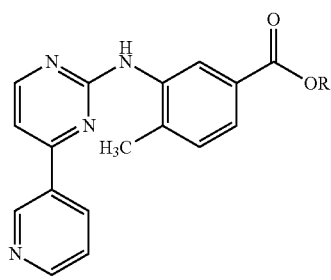

with an aniline 5-(4-methyl-1H-imidazol-1-yl)-3-(trifluoromethyl)-benzenamine of the following structure:

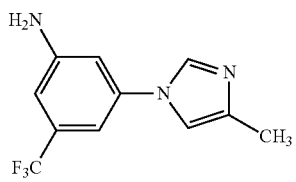

wherein R is lower alkyl, phenyl, phenyl-lower alkyl or substituted phenyl, wherein the method is promoted by a trialkyl aluminum compound and carried out in an organic solvent. Lower alkyl comprises $C_1$ to $C_{10}$ alkyl, preferably $C_1$ to $C_6$, more preferably $C_1$ to $C_3$. The method is carried out at temperature between 45° C. to 115° C., the alkyl group of the trialkyl aluminum compound is methyl or ethyl, and the organic solvent is selected from the group consisting of tetrahydrofuran, dimethylformamide, toluene, and other aromatic hydrocarbons.

In a preferred embodiment of the present invention, the ester is ethyl 4-methyl-e-[[4-(3-pyridinyl)-2-pyrimidinyl]amino]benzoate of the following structure:

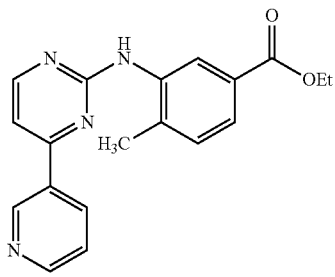 [SMILES: CCOC(=O)c1ccc(C)c(Nc2nccc(-c3cccnc3)n2)c1]

In another preferred embodiment of the present invention, the coupling reagent trialkyl aluminum compound is trimethyl aluminum. In another preferred embodiment of the present invention, the organic solvent is toluene.

The reaction scheme of one preferred embodiment is illustrated as follows:

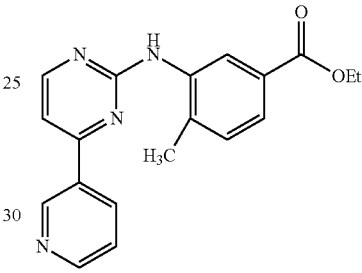

ethyl 4-methyl-3[[4-(3-pyridinyl)-2-pyrimidinyl]amino]benzoate

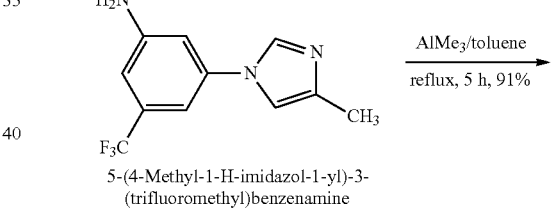

5-(4-Methyl-1-H-imidazol-1-yl)-3-(trifluoromethyl)benzenamine

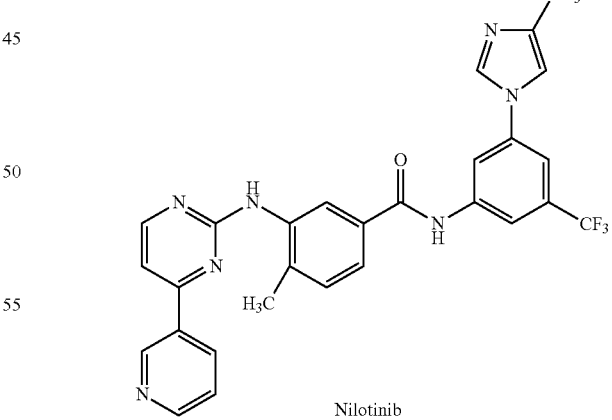

Nilotinib

The singular forms "a," "an," and "the" include the plural forms unless the context clearly dictates otherwise. The term "includes" means "comprises." Unless the context dictates otherwise, the term "coupled" means mechanically, electrically, or electromagnetically connected or linked and includes both direct connections or direct links and indirect connections or indirect links through one or more intermediate elements not affecting the intended operation of the described system.

Unless otherwise indicated, all numbers expressing quantities of components, percentages, temperatures, times, and so forth, as used in the specification or claims are to be understood as being modified by the term "about" or "approximately." Accordingly, unless otherwise indicated, implicitly or explicitly; numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

EXAMPLES

The examples below are non-limiting and are merely representative of various aspects and features of the present invention.

Example 1

A three-necked 250 mL round bottom flask equipped with thermometer, condenser, and stir bar, was charged with toluene (75 mL), ethyl 4-methyl-3-[[4-(3-pyridinyl)-2-pyrimidinyl]amino]benzoate (3 g, 9.0 mmol, 1 eq.), and 5-(4-methyl)-1H-imidazol-1-yl)-3-(trifluoromethyl)benzenamine (2.82 g, 11.7 mmol, 1.3 eq.). The suspension was warmed up and 6.8 mL AlMe$_3$ (2 M in toluene, 13.8 mmol, 1.5 eq.) was added. The entire mixture was then being refluxed for 5 hrs until the ester disappeared and the process was monitored by an HPLC. After the mixture was cooled down, excess trimethyl aluminum was quenched with aqueous sodium hydroxide. The product was isolated by filtration and dried under vacuum affording 4.32 g (91%) nilotinib with 99.3% purity (HPLC). Results of other examples with different ratio of starting material are listed in the Table 2.

TABLE 2

Examples of the reaction

| entry | Eq. ester/aniline | Coupling Reagent | Time (h) | Nilotinib (Area %) (By HPLC) | ester (Area %) (By HPLC) |
|---|---|---|---|---|---|
| 1 | 1.0/1.1 | 2M AlMe$_3$ (1.5 eq.) | 1.0 | 81.55 | 11.28 |
|   |         |                       | 3.0 | 93.39 | 2.17 |
|   |         |                       | 5.0 | 95.53 | 0.88 |
|   |         |                       | 6.0 | 95.68 | 0.66 |
| 2 | 1.0/1.2 | 2M AlMe$_3$ (1.5 eq.) | 1.0 | 86.48 | 6.11 |
|   |         |                       | 3.0 | 93.40 | 1.07 |
|   |         |                       | 5.0 | 94.57 | 0.20 |
|   |         |                       | 6.0 | 94.60 | 0.15 |
| 3 | 1.0/1.3 | 2M AlMe$_3$ (1.5 eq.) | 3.0 | 93.89 | 2.05 |
|   |         |                       | 5.0 | 95.10 | 0.99 |
|   |         |                       | 6.0 | 95.61 | 0.50 |

What is claimed is:

1. A method for preparing Nilotinib of the following structure:

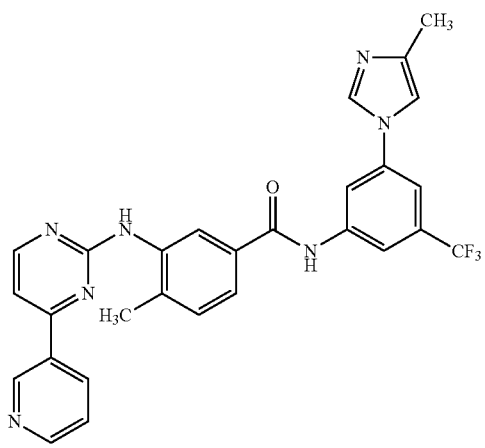 [SMILES: Cc1cn(-c2cc(NC(=O)c3ccc(C)c(Nc4nccc(-c5cccnc5)n4)c3)cc(C(F)(F)F)c2)cn1]

comprising reacting an ester of the following structure:

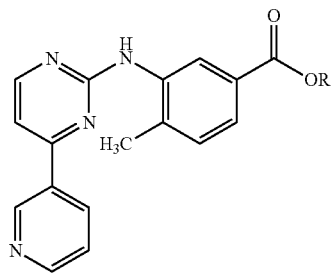

with an aniline 5-(4-methyl-1H-imidazol-1-yl)-3-(trifluoromethyl)-benzenamine of the following structure:

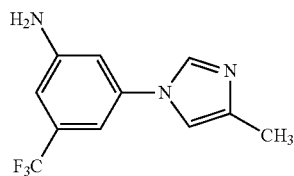

wherein R is lower alkyl, phenyl, phenyl-lower alkyl or substituted phenyl,
wherein the reaction is promoted by a trialkyl aluminum compound in an organic solvent.

2. The method of claim 1, wherein R is an ethyl group or a methyl group.

3. The method of claim 1, wherein the trialkyl aluminum compound is trimethyl aluminum.

4. The method of claim 1, wherein the organic solvent is selected from the group consisting of tetrahydrofuran, dimethylformamide, toluene, and other aromatic hydrocarbons.

5. The method of claim 1, wherein the organic solvent is toluene.

* * * * *